United States Patent [19]

Hilal

[11] Patent Number: 5,192,290
[45] Date of Patent: Mar. 9, 1993

[54] EMBOLECTOMY CATHETER

[75] Inventor: Said Hilal, Laguna Niguel, Calif.

[73] Assignee: Applied Medical Resources, Inc., Laguna Hills, Calif.

[21] Appl. No.: 574,648

[22] Filed: Aug. 29, 1990

[51] Int. Cl.$^5$ ............................................. A61M 1/00
[52] U.S. Cl. ........................................ 606/159; 604/1; 606/194
[58] Field of Search ................ 604/1, 11, 268, 275, 604/280, 96, 104, 2, 267; 606/159, 192, 194, 198; 128/756, 757, 759

[56] References Cited

U.S. PATENT DOCUMENTS

| | | |
|---|---|---|
| 2,490,168 | 12/1949 | Strauss .................................... 604/2 |
| 3,435,829 | 4/1969 | Fogarty . |
| 3,467,101 | 9/1969 | Fogarty . |
| 3,640,282 | 2/1972 | Kamen et al. ........................ 604/96 |
| 3,799,173 | 3/1974 | Kamen ................................. 604/91 |
| 3,877,464 | 4/1975 | Vermes ............................... 128/759 |
| 3,896,815 | 7/1975 | Fettel et al. .......................... 606/194 |
| 3,923,065 | 12/1975 | Nozick . |
| 3,978,863 | 9/1976 | Fettel et al. .......................... 606/192 |
| 3,996,938 | 12/1976 | Clark . |
| 4,385,635 | 5/1983 | Ruiz . |
| 4,531,943 | 7/1985 | Van Tassel . |
| 4,564,014 | 1/1986 | Fogarty . |
| 4,735,214 | 4/1988 | Berman ............................... 128/759 |
| 4,810,543 | 3/1989 | Gould . |
| 4,877,037 | 12/1989 | Ko et al. .............................. 128/757 |
| 4,886,493 | 12/1989 | Yee ....................................... 604/54 |
| 4,890,612 | 2/1990 | Kensey ................................ 623/1 |
| 4,968,298 | 11/1990 | Michelson ........................... 604/73 |
| 5,011,488 | 4/1991 | Ginsburg ............................ 606/159 |
| 5,085,633 | 2/1992 | Hanifl et al. ........................ 604/73 |

FOREIGN PATENT DOCUMENTS

| | | | |
|---|---|---|---|
| 3519626 | 12/1986 | Fed. Rep. of Germany | 606/159 |
| 395076 | 3/1970 | U.S.S.R. | 606/159 |

OTHER PUBLICATIONS

"Balloon Embolectomy Catheter Used Percutaneously", by Zimmerman et al., *Radiology*, vol. 158, No. 1, Jan. 1986.

Primary Examiner—Stephen C. Pellegrino
Assistant Examiner—Ralph A. Lewis
Attorney, Agent, or Firm—Richard L. Myers

[57] ABSTRACT

An improved embolectomy catheter, includes a catheter body, an elastomeric foam catheter tip attached at one end of the catheter body, and actuator means for elastically deforming the catheter tip. The catheter tip deforms longitudinally and radially in response to activation of the actuation means. The catheter tip may be formed of any type of sterile elastomeric foam, which may be easily compressed and restored to its original shape upon decompression.

12 Claims, 6 Drawing Sheets

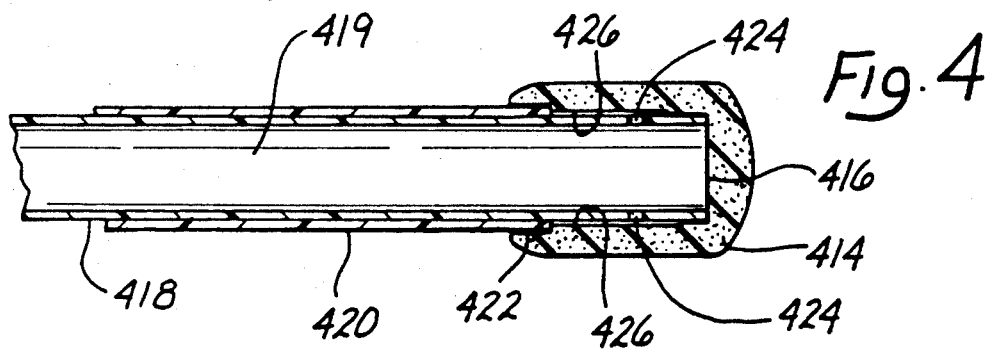
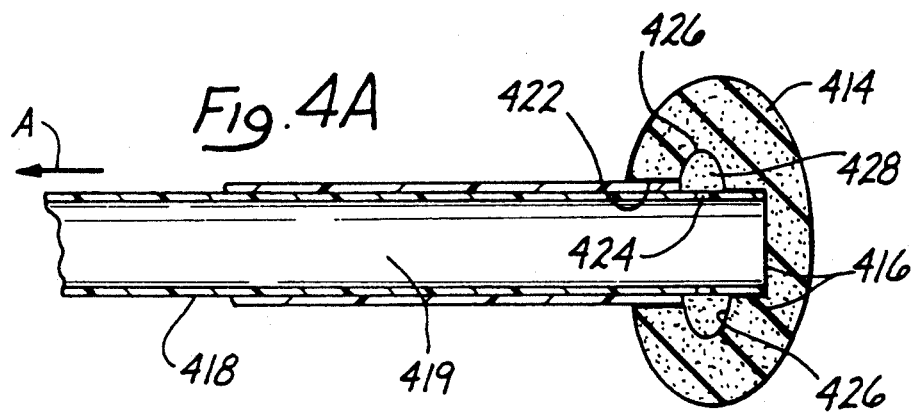
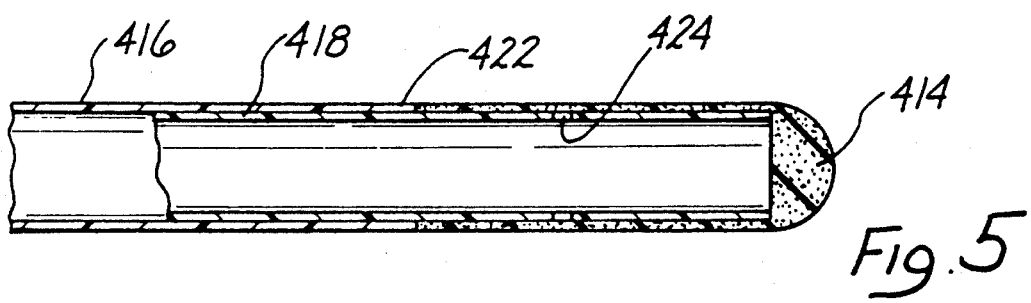
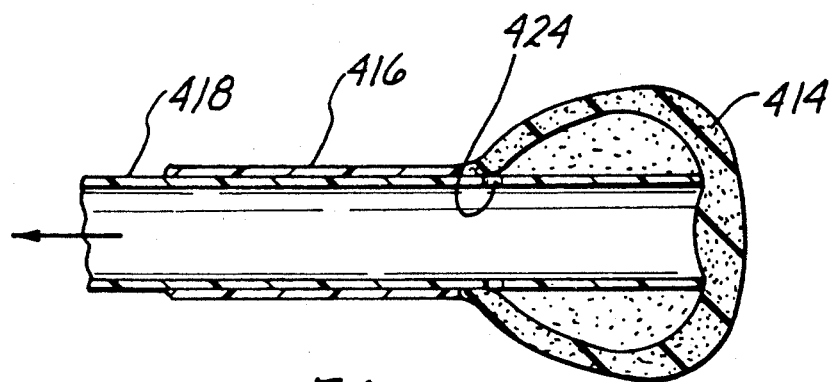

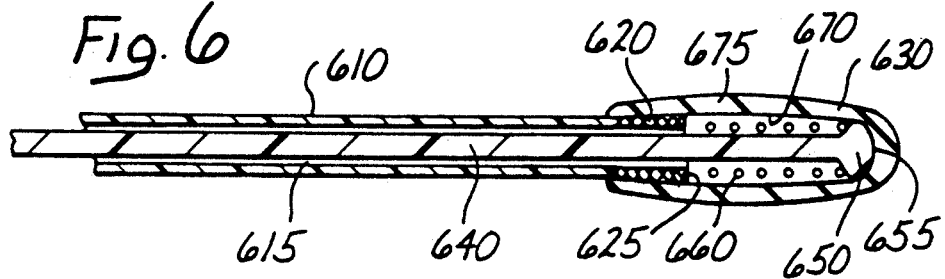
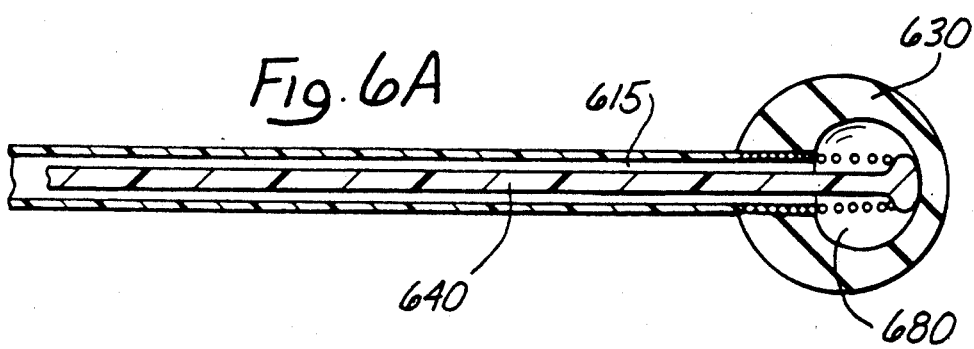
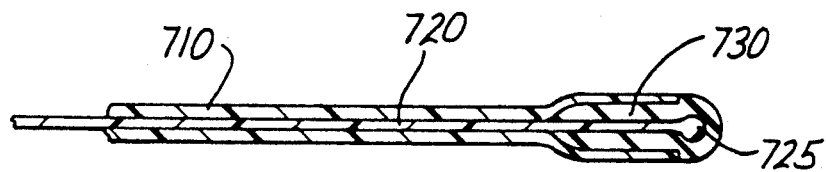
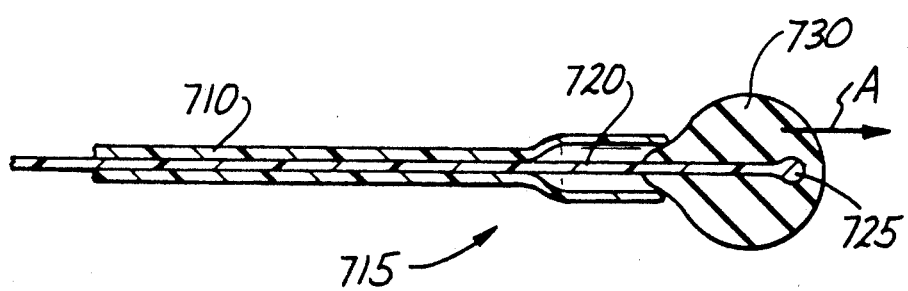

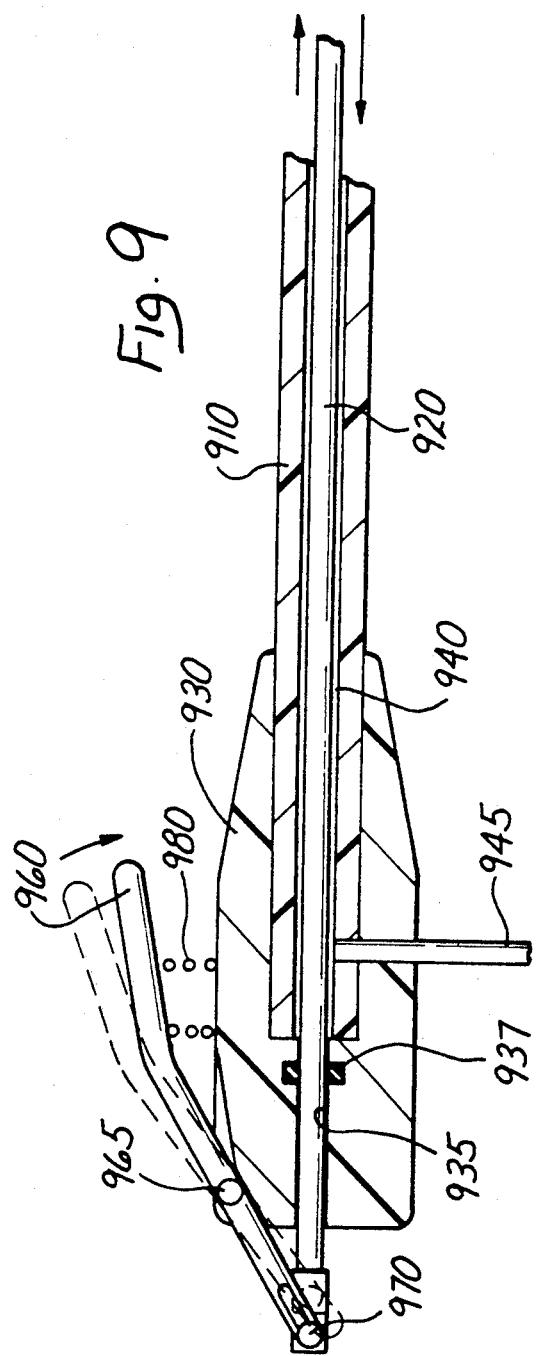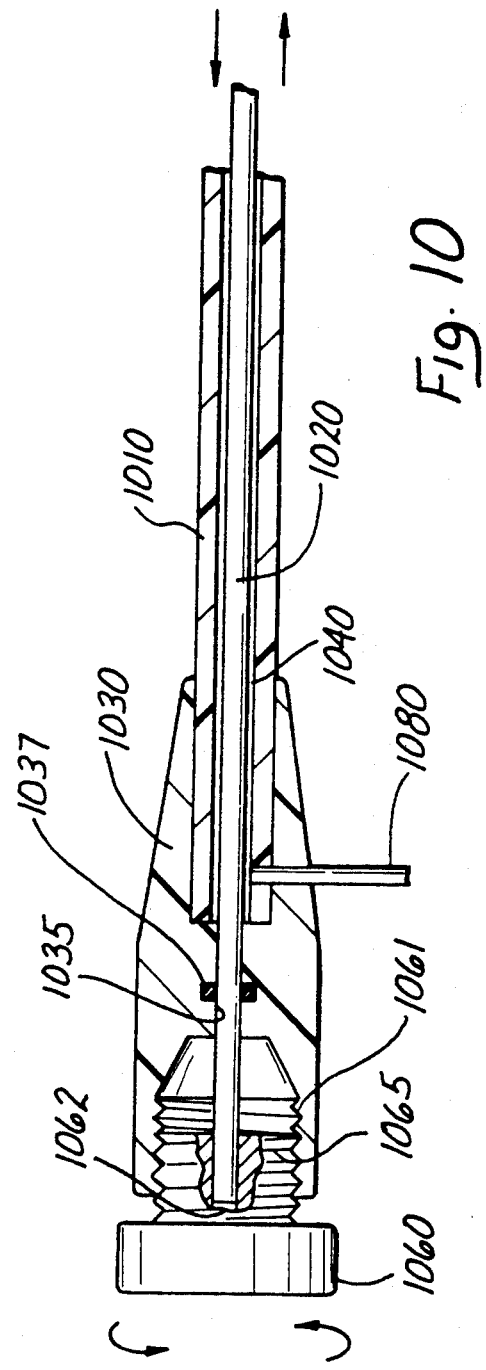

EMBOLECTOMY CATHETER

The present invention relates to catheters for medical and surgical application and, more specifically, to an embolectomy catheter having a deformable elastomeric foam tip for removing blood clots.

For many years, inflatable balloon embolectomy catheters, also referred to in the medical profession as "balloon catheters" or "Fogarty catheters", have been used in vascular surgical procedures to remove blood clots from a patient's blood vessels. Use of the embolectomy catheter in vascular surgery has saved literally thousands of arms and legs which might otherwise have required amputation.

A typical inflatable embolectomy catheter is disclosed in U.S. Pat. No. 3,435,826, issued Apr. 1, 1969 to Thomas Fogarty, and incorporated herein by reference. This patent discloses a balloon catheter in which the balloon material is longitudinally stretched when deflated causing the balloon to contract circumferentially and thereby smoothly hug the catheter body. Other such typical devices are disclosed in the U.S. Pat. No. 4,403,612, issued Sep. 13, 1983 to Thomas Fogarty, and U.S. Pat. No. 3,467,101 issued Sep. 6, 1969 also the Thomas J. Fogarty. These references are likewise incorporated herein by this reference.

An embolectomy catheter is used to remove emboli and thrombus from the veins and arteries of the body. These emboli typically form around the valves of the heart as a small blood dislodged thereby permitting them to follow the blood flow into the extremities of the body. This can be particularly dangerous if the clot is transmitted to the brain where it can result in a stroke. More typically however, the emboli flows into a peripheral artery which becomes progressively smaller until the emboli lodges. In this stationary location, the clot is commonly referred to as a thrombus. Emboli can also form in the veins of the body where they tend to lodge as thrombus around the venous valves.

Over time a thrombus will become increasingly larger until it totally blocks blood flow to the extremity. Although the veins carry blood away from the extremities and back to the heart, a thrombus in the veins typically creates a back pressure in the circulatory system so as to reduce blood flow even in the arterial system. Reduced blood flow in the extremities of course denies those regions with the oxygen which is necessary to maintain the tissue. Ultimately, amputation may be required.

In a process for removing a thrombus or clot using an embolectomy catheter, the location of the clot is determined using fluoroscopy, and an incision is made in the vessel containing the clot or in a branch leading to the clotted vessel. The embolectomy catheter is inserted through the incision and directed through the vessel or branch leading to the clot. With the balloon deflated, the distal tip of the catheter containing the balloon is carefully moved through the clot. The balloon is then inflated on the distal side of the clot and the catheter gradually withdrawn. In this procedure, the balloon acts as a drag to push the clot ahead of the balloon. As the catheter is withdrawn, the clot reaches the region of incision where it can be readily removed from the vessel. This insertion and removal process is typically repeated until the vessel is cleared of all clot material.

Thrombus can occur in many vessels of the body including those which are relatively normal as well as those which are diseased. Atherosclerosis is by far the most common disease affecting blood vessels. This disease causes the vessels to become quite tortuous, having regions of marked angulation and narrowing attributed to the growth of atherosclerotic plaque. Under such conditions, clots occurring in the diseased vessels resist the passage of conventional, relatively straight and stiff catheters. If undue force is exerted, the catheter may pass through the vessel wall or cause the atherosclerotic plaque to be dislodged.

Many difficulties attend the removal of clots with balloon catheters. During the dragging of a clot along the vessel, resistance often causes the balloon portion of the catheter to slide over the tip of the catheter. Oftentimes, it becomes necessary to reduce the inflation of the balloon when the catheter is withdrawn. During such deflation, the distal end portion of the balloon may become distended over the catheter tip causing the tip to angulate acutely. This can result in trapping fluid in the distal end portion of the balloon which ultimately impairs deflation of the balloon.

Other problems also exist. Arteries and veins exhibit certain anatomical differences. Arteries are relatively thick walled vessels lacking valves. Veins, which primarily function to return anoxic blood to the heart, are thin walled vessels containing numerous valves which assist the blood flow returning to the heart. Hence, catheters designed for the extraction of venous emboli must be more pliable in order to avoid perforation of the venous wall and to permit the catheter to be atraumatically moved through the valves.

Another problem with balloon catheters is the possibility of damage to the delicate intimal lining of the arteries and veins. In the past, the pressures associated with fluid filled balloons have created significant shear forces on the intimal lining as the catheter has been moved through the vessel. Unfortunately, these pressures have been sufficient in some cases to strip the intimal lining from the wall. The tearing or damaging of the intimal lining is extremely undesirable as it may result in adverse physiological consequences.

In other situations, plaque associated with atherosclerotic disease has formed along the interior surfaces of the arteries and veins. As a balloon catheter is dragged through the vessel, the balloon portion may catch on protrusions of this accumulated plaque. If the balloon catches upon the plaque, the balloon can become deformed such that stress forces are inadvertently applied to the plaque protrusion. Such a stress force may be sufficient to dislodge or shear off the plaque creating even further emboli with severely adverse consequences. The balloon may also rupture with the possibility of leaving balloon fragments in the blood stream.

Hence, a need exists for an embolectomy catheter for removing thrombus without damaging the intimal lining or causing any other traumatic injury to the arteries or veins, and for providing a catheter tip which will not present the risks of balloon overinflation or rupture.

SUMMARY OF THE INVENTION

The present invention is directed to a catheter, which includes a catheter body, an elastomeric foam or other compressible material attached at a distal tip of the catheter body, and a catheter tip actuator, which elastically deforms the compressible material. When actuated, the catheter tip longitudinally deforms in response to activation of the actuation means. The catheter tip may be formed of any type of sterile elastomeric foam or other material which can be easily compressed and restored to its original shape upon decompression.

The present invention is particularly advantageous because it materially reduces the risk that plaque will be sheared off of the vessel walls thereby damaging the intimal lining of the vessel.

BRIEF DESCRIPTION OF THE DRAWINGS

FIG. 4 is a cross-sectional view of another embodiment of the embolectomy catheter of the present invention illustrated in its low profile state.

FIG. 4A is a cross-sectional view of the embodiment of the embolectomy catheter shown in FIG. 4, with the catheter illustrated in its actuated state.

FIG. 5 is a cross-sectional view of a further embodiment of the embolectomy catheter of the present invention, illustrating the catheter in an insertion state.

FIG. 5A is a cross-sectional view of the catheter illustrated in FIG. 5 with the catheter shown in an expanded, operative state.

FIG. 6 is a cross-sectional view of yet another embodiment of the embolectomy catheter of the present invention.

FIG. 6A is a cross-sectional view of the embolectomy catheter of FIG. 6, showing the configuration of the catheter when the stylet has been retracted and gas or liquid has been introduced into the lumen.

FIG. 7 shows yet another embodiment of the embolectomy catheter of the present invention.

FIG. 7A shows the embolectomy catheter of FIG. 7 in an activated condition, with the control stylet extended.

FIG. 9 is a cross-sectional view of another embodiment of an actuator, which may be used with the catheters of the present invention.

FIG. 10 is a cross-sectional view of a further embodiment of an actuator for use with embolectomy catheters of the present invention.

DETAILED DESCRIPTION OF THE DRAWINGS

Figure 1:
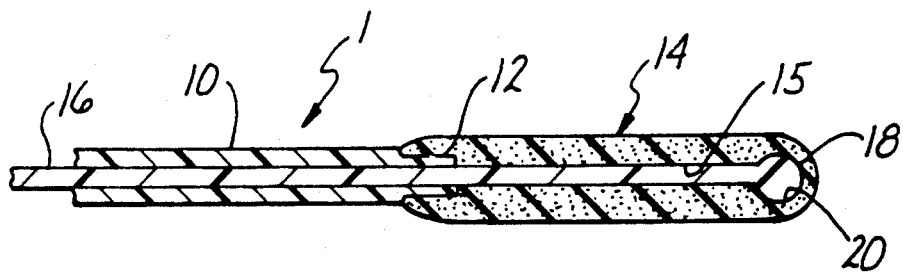
FIG. 1 is a cross-sectional view of one embodiment of the embolectomy catheter of the present invention.
Figure 1A:
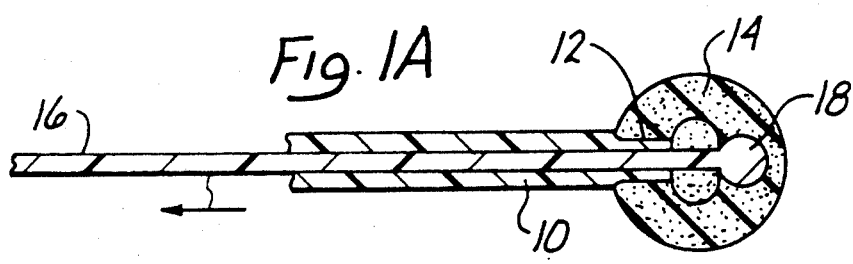
FIG. 1A depicts the catheter of FIG. 1 with a control stylet retracted.

An embolectomy catheter of the present invention is illustrated in FIG. 1 and designated generally by the reference numeral 1. Catheter body 10 is an elongated flexible tube having a length of choice, typically less than 100 centimeters, depending on the distance from the incision in the vessel to the location of the blood clot to be removed. The entire length of the catheter body 10 is not shown in FIG. 1. Catheter body 10 has a recessed end portion 12. A foam tip 14 having an inner surface 15 is bonded at its proximal end to the recessed end 12 of the catheter body 10, using any conventional, non-toxic bonding material. The foam tip 14 may be formed of any suitable biocompatible, elastomeric material, such as silicon rubber foam. The case of a foam material, the foam may be either closed or open cell, but open cell foam is preferred. A control stylet 16, having a rounded portion 18, runs through the entire length of the catheter body 10 and foam catheter tip 14. The rounded stylet tip portion 18 is bonded to the end of an interior surface 20 of the foam catheter tip 14 using a conventional, non-toxic adhesive.

Figure 2A:
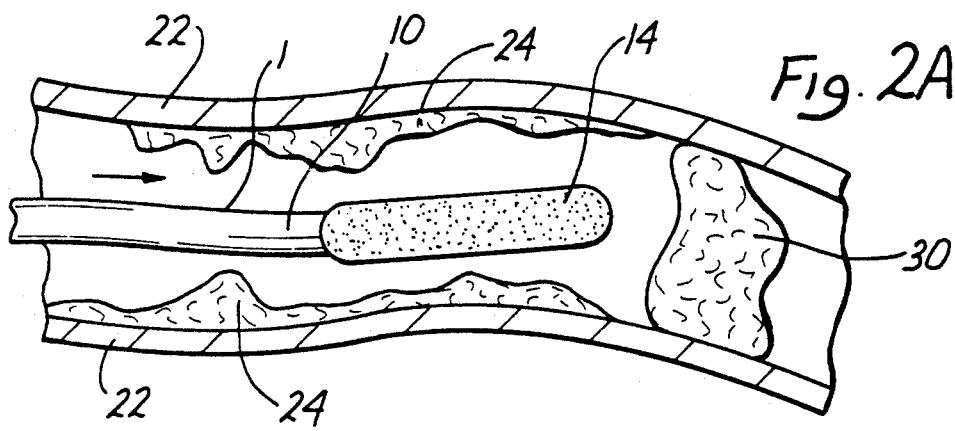
FIGS. 2A through 2C illustrate one embodiment of the embolectomy catheter of the present invention operatively positioned within a blood vessel.
Figure 2B:
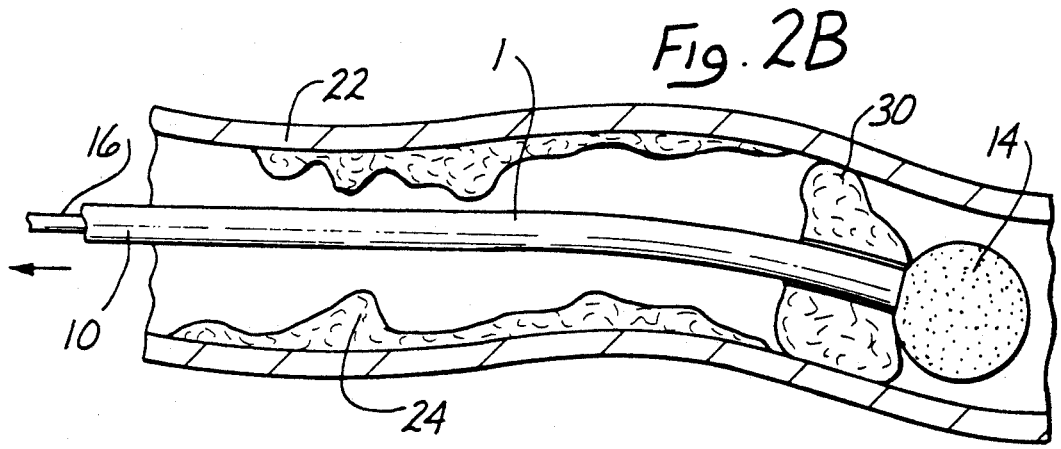
Figure 2C:
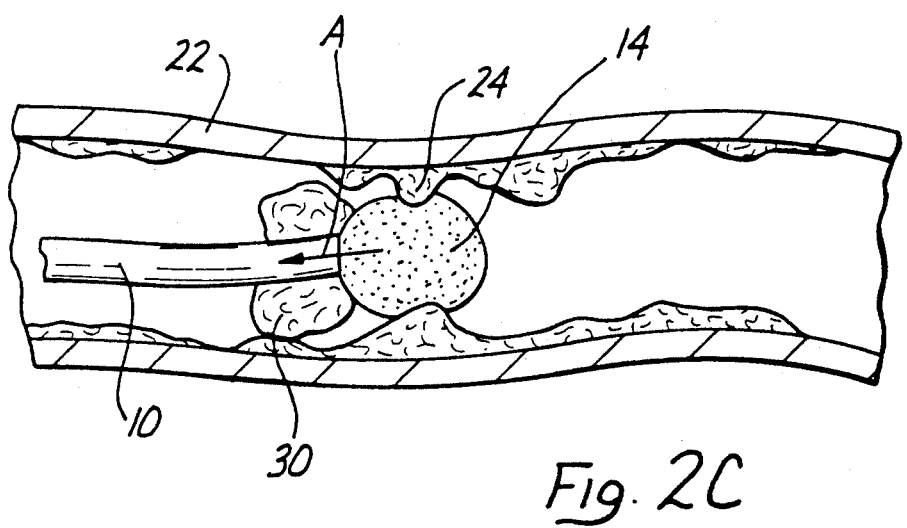

FIGS. 2A through 2C illustrate one embodiment of the embolectomy catheter of the present invention in operation. Referring to FIG. 2A, embolectomy catheter 1 is inserted into a blood vessel 22 which may be either an artery or a vein. The vessel 22 is illustrated in a diseased state in that portions of its interior walls are covered by an atherosclerotic material commonly referred to as plaque 24. The plaque 24 is not uniform in shape and typically contains numerous jagged portions. A thrombus or clot 30 to be removed is lodged in vessel 22. Catheter 1, in its deflated state, is fed through the artery 22 toward the location of embolus 30 as shown in FIG. 2A.

Referring to FIG. 2B, catheter 1 is fed through and past embolus 30, so as to position catheter tip 14 behind the mass of embolus 30. With the catheter body 10 held in place, the control stylet 16, is retracted in the proximal direction, the direction of the incision, so as to deform the catheter tip 14 into a roughly spherical shape.

The entire catheter 1, with the catheter body 10, stylet 16, and catheter tip 14, is withdrawn through the vessel 22, in the direction of arrow A illustrated in FIG. 2C. As the deformed spherical tip 14 is pulled proximally through the vessel, it pushes the clot 30 in front of it toward the incision where it can be removed. The clot 30 is essentially captured by the foam balloon 14 and dragged along with the catheter 1 as it is withdrawn from the artery 22.

As illustrated in FIG. 2C, the unique foam catheter tip 14 uniformly deforms upon contact with the jagged and irregular surface of the plaque 24. Because of the unique compressible properties of elastomeric foam, deformation of the tip 14 yields uniform pressure about the interior surface of the diseased vessel 14; hence, shear forces which might dislodge the plaque and damage the vessel are minimized.

Figure 3:
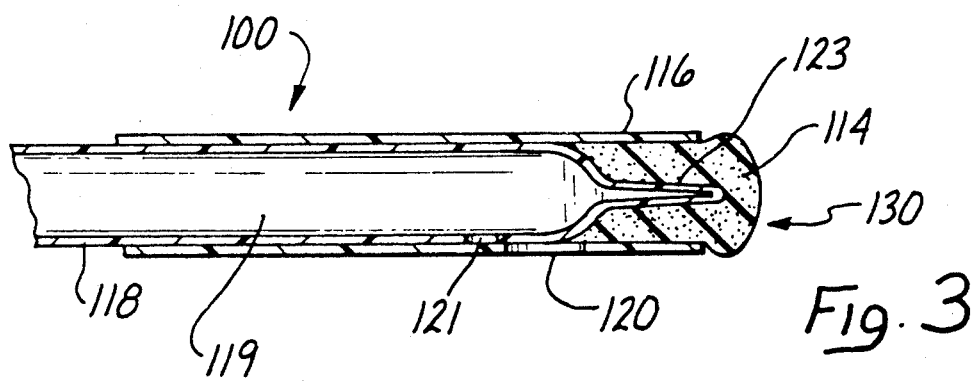
FIGS. 3 and 3A illustrate a cross-sectional view of another embodiment of the embolectomy catheter of the present invention, shown in its retracted, compressed state.

FIG. 3 is a cross-sectional view of another embodiment of the embolectomy catheter of the present invention. Catheter 100 consists of an outer catheter body tube/sheath 116, which extends the length of the entire catheter 100. An inner catheter tube 118 defines a lumen 119 and is slidable within the entire length of the outer catheter body tube/sheath 116. The outer catheter body tube/sheath 116 has a slot 120 cut into its surface proximate to catheter end 130. The inner tube 118 likewise has an infusion/sampling port 121 located approximate to end 130. When outer catheter body tube/sheath 116 is disposed with the foam catheter tip 114 in its initial compressed state, as shown in FIG. 3, the outer catheter body tube/sheath 116 covers the infusion/sampling port 121.

The foam catheter tip 114 is bonded, using a non-toxic bonding adhesive, to a recessed, perhaps printed, end 123 of gas/fluid lumen 118. The foam catheter tip 114 may be formed of any suitable, biocompatible elastomeric foam, such as silicone rubber foam. The foam catheter tip 114 is initially at least partially enclosed within a compressed by the end of outer catheter body tube/sheath 116.

Figure 3A:
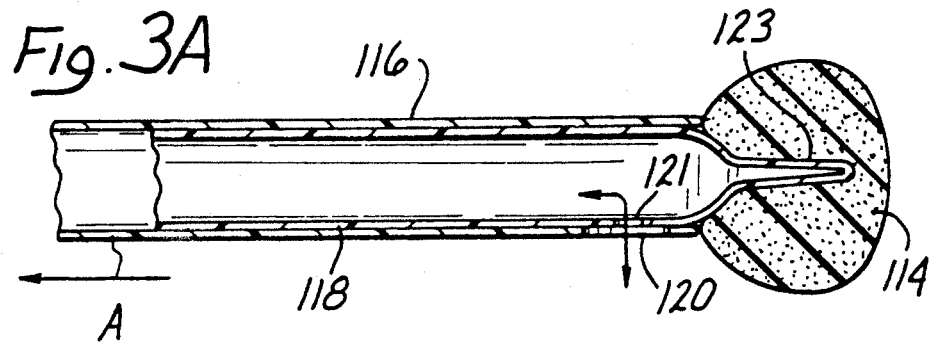

FIG. 3A is a cross-sectional view of the catheter, shown in FIG. 3, in its decompressed state. After the catheter has been positioned distal to the clot 22 to be removed, the outer catheter body tube/sheath 116 is retracted in the direction indicated by arrow A, as shown in FIG. 3A. This enables the foam catheter tip 114 to expand to its natural, essentially spherical shape. When the outer catheter body tube/sheath 116 is retracted, the infusion/sampling port 121 of the central lumen 118 is coincident with the slot 120 in outer tube 116, so as to enable infusion or sampling through a central lumen 119. In these embodiments of FIG. 3 and FIG. 3A the inner catheter tube 118 functions as the stylet 16 except that it provides the central lumen 119 for infusion or sampling.

FIG. 4 is a cross-sectional view of another embodiment of the embolectomy catheter of the present invention. Outer tube 420 has a foam balloon catheter tip 414 attached by an adhesive at end 422. The foam balloon catheter tip 414 may be formed of any biocompatible, elastomeric material, such as silicone rubber foam. An inner central tube 418 is received within outer tube 420 and runs the length of the entire catheter. Inner central tube 418 is attached at its end 416 to the interior end surface of foam catheter tip 414. An adhesive secures the end 416 of central lumen 418 to the interior end surface of catheter tip 414. In this particular embodiment, the inner surface 426 of foam catheter tip 414 is nonporous. Inflation ports 424 are provided in the central tube 418 and extend from lumen 419 into proximity to the interior nonporous surface 426 of catheter tip 414.

FIG. 4A is a cross-sectional view of the FIG. 4 embodiment with the embolectomy catheter illustrated in an actuated state. The central tube 418 is retracted relative to the outer tube 416 in the direction of the incision, indicated by arrow A. This retraction results in deformation of the interior surface of foam tip 414 forming an interior cavity 428. Gas or fluid is supplied through the central lumen 419 and exits into the interior cavity 428. In this particular embodiment, introduction of the gas or fluid into the cavity 428 results in increasing the pressure of the foam tip 414 against the walls of the vessel. Under particular circumstances this may be desirable in order to maintain an adequate seal with the walls as the tip 414 pushes the clot 30 through the vessel. When actuated, the catheter tip 414 is approximately ellipsoid in shape, as shown in FIG. 4A.

The embodiment illustrated in FIGS. 4 and 4A also functions in another manner. If the foam tip 414 is provided with a natural, low profile shape as illustrated in FIG. 4, the introduction of fluid into the cavity 428 can result in an expansion of the foam tip 414 beyond the natural state to the enlarged shape illustrated in FIG. 4A.

The embodiment of FIG. 5 is similar to that of FIG. 4 except that the foam catheter tip 414 is shown with a lower profile in its initial insertion state. In this aspect of the invention, no portion of the foam tip 414 has a diameter greater than the diameter of the outer tube 416. In a preferred embodiment, the entire length of the foam tip 414 in the low profile state is generally equal to the diameter of the outer tube 416. FIG. 5A illustrates the catheter of FIG. 5 in a retracted, expanded state.

FIG. 6 is a cross-sectional view of yet another embodiment of the embolectomy catheter of the present invention. Catheter body tube 610 is bonded at its end 620 with an adhesive to a foam catheter tip 630. The interior surface 670 of foam balloon tip 630 is nonporous. A stylet 640 is provided with a diameter substantially smaller than the interior diameter of catheter body tube 610 except at its distal end where it is enlarged to form a rounded tip portion 650. This stylet 640 is received through catheter body tube 610 and runs the length of catheter body tube 610. The rounded end tip portion 650 of stylet 640 is bonded at end 655 to the interior end surface of foam tip 630. A coil spring 660 can be provided to surround the stylet 640 between stylet tip 650 and an end 625 of catheter body tube 610. This spring 660 can be elongated beneath the foam tip 630 so that space is created between adjacent convolutions of the spring. This space communicates with a central lumen 615 which is defined between the interior surface of the catheter body 610 and the exterior surface of stylet 640. A gas or other fluid can be introduced through this lumen 615 and the spaced convolutions of spring 660 to expand the foam tip 630 in the manner previously discussed with reference to FIG. 4.

FIG. 6A is a cross-sectional view of the embolectomy catheter of FIG. 6, showing the configuration of the catheter when stylet 640 has been retracted and gas or liquid has been introduced into the lumen 615. The stylet 640 is retracted proximally, as indicated by arrow A. In a preferred embodiment the foam balloon 630 is deformed into an essentially spherical shape. Gas or fluid is introduced into the lumen 615 and pumped into a chamber 680, which is defined by the deformation of the interior surface 670 of foam balloon 630. Introduction of gas or fluid into the interior chamber 680 provides a uniform pressure which facilitates expansion of the foam balloon 630 and further reduces the possibility of distortion or deformation of the catheter tip 630 as the catheter is drawn through the vessel.

FIG. 7 shows yet another embodiment of the embolectomy catheter of the present invention. Catheter body 710 has a unique, enlarged end portion 715 at one end. A control stylet 720 is received in catheter body 710 and runs the length of the catheter body 710. The rounded tip 725 of control stylet 720 is bonded, by an adhesive, to a foam tip 730. The foam tip 730 may be formed of any biocompatible, elastomeric foam, such as silicone foam rubber. A length of the end portion of the control stylet is likewise bonded to the interior surface of the silicone foam tip 730. In its low profile state, the foam tip 730 is stored, in a compressed state, within the enlarged end 715 of catheter body 710.

FIG. 7A shows the embolectomy catheter of FIG. 7 in an activated, expanded state with control stylet 710 moved distally relative to the body 710 in the direction indicated by arrow A. This operation of the stylet 710 pushes the tip 730 from the end portion 720 of the body 710. Thus deployed the foam tip 730 decompresses to its expanded natural shape. The catheter is then withdrawn through the blood vessel to complete the embolectomy procedure.

A number of actuation mechanisms can be provided to facilitate a change in the foam tip from the low profile state to the expanded state. Typically these mechanisms are located at the proximal end of the catheter, the end opposite that of the foam tip. As noted from discussion of the numerous embodiments of the embolectomy catheter of the present invention, the foam balloon catheter tip is actuated by either the retraction or extension of a control stylet, or the retraction or extension of a catheter body sheath.

Figure 8:
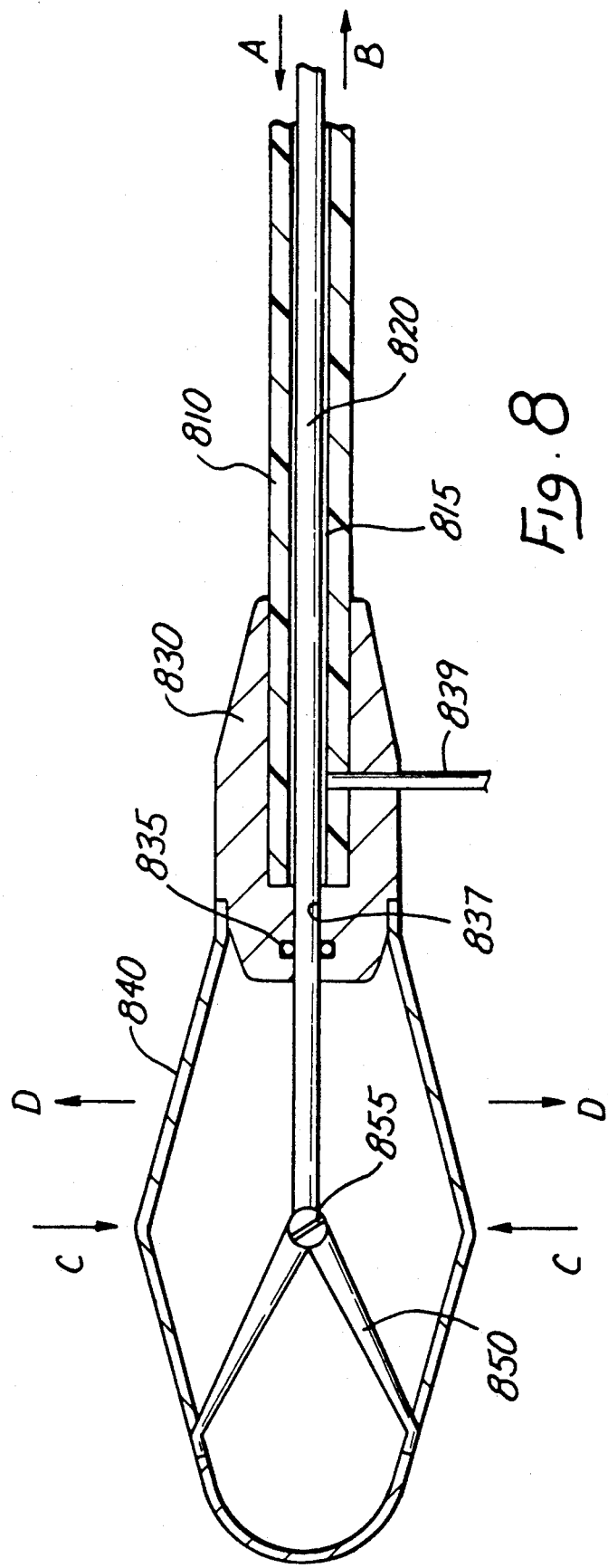
FIG. 8 shows one embodiment of an actuator which may be used to extend or retract the control stylet in several of the catheter embodiments previously illustrated.

FIG. 8 shows one actuator embodiment which may be used to extend or retract a control stylet 820, which is used in a number of the catheter embodiments of the present invention. An actuator body 830 is attached to catheter body tube 810. The control stylet 820 is likewise received through the actuator body 830 and a center bore 837. A lumen seal ring 835 seals the end of the actuator housing 830. A side port 839 through the actuator body 830 provides access to a gas/fluid lumen 815 in the catheter body tube.

A control grip 840 is attached to actuator body 830. Control grip 840 has two scissor hinges 850 pivotally attached to the end of the control stylet 820 by pivot bearing 855. When pressure is applied to the control grip 840, for example in the direction of arrow C, the scissor hinges 850 close, thereby causing the control stylet 820 to extend in the direction of arrow B. When the control grip 840 is released, or force is applied in the direction of arrow D, the control stylet 820 retracts in the direction of arrow A. Hence by compressing or decompressing the control 840, the surgeon may expand or contract the foam tip, such as the tip 14 shown in FIG. 1. It should be noted that the actuator device illustrated in FIG. 8 may be used with any of the embolectomy catheter embodiments of the present invention which use a control stylet as the means for actuating the foam balloon.

FIG. 9 is a cross-sectional view of another embodiment of the actuator, which may be used with the present invention. Catheter body tube 910 is received into and attached to actuator body 930. The control stylet 920 is received through bore 935 in actuator body 930. An inner lumen seal ring 937 is placed in a recess in actuator body 930, to create a seal between the actuator body 930 and the stylet 920. A lumen access port 945 runs through the actuator body 930 and provides ingress and egress to the central lumen 940 in the catheter body tube 910. An actuator lever 960 is pivotably attached to the actuator body 930 by a pivoting joint 965. The end of actuator lever 960 is slidably attached to the end of control stylet 920 by a slide bearing 970. The control lever 960 is attached to a biasing spring 980, which runs coextensively between the surface of actuator body 930 and the underside of actuator lever 960.

To extend or retract control stylet 920, the surgeon grasps actuator body 930 and pivots the control lever either away from actuator body 930 to extend control stylet 920 or toward actuator body 930 to retract control stylet 920.

FIG. 10 is a cross-sectional view of yet another embodiment of an actuator for use with any one of the embodiments of the present embolectomy catheter having a control stylet. Catheter body tube 1010 is received in actuator body 1030. A bore 1035 runs radially through the actuator body 1030 and receives control stylet 1020 therethrough. A lumen inner seal ring 1037 creates a seal between gas fluid lumen 1040 and catheter body 1030. A rotation expansion control knob 1060 has a threaded portion 1065, which is rotatably received into a threaded portion 1061 of the activator body 1030. The control stylet 1020 is rotatably attached to the control knob 1060 by pivot bearing 1062.

To retract the control stylet 1020, the expansion control knob 1060 is rotated in a counter clockwise direction. To extend the control stylet 1020, the surgeon rotates the expansion control knob 1060 in a clockwise direction.

Any of the actuation mechanisms illustrated in FIGS. 8, 9 or 10 can be adapted for use with the catheter embodiments of FIGS. 1 and 4-7. These mechanisms can all be mounted to provide relative axial movement between an outer catheter such as the catheter body 10 and any inner member, such as the stylet 16 of FIG. 1 or the inner tube 118 of FIG. 3. The mechanisms are typically mounted on the outer catheter and operable to move the inner stylet or tube axially within the outer tube. This operation either deploys or retracts the foam tip, such as the tip 14 in the FIG. 1 embodiment, in the manner previously described.

Although the invention has been described with reference to specific embodiments various changes may be made in the details of construction and arrangement of parts. All such modifications within the scope of the appended claims are included in the invention.

I claim:
1. A catheter comprising:
   a flexible tubular nondistensible catheter body having first and second ends;
   an elastomeric nonwoven foam catheter tip attached to and extending outwardly from the catheter body at the first end;
   a retractable flexible stylet extending through said catheter body and being attached to said catheter tip;
   wherein operation of said stylet at said second end of the catheter body deforms said elastomeric foam catheter tip at said first end of the catheter body.

2. The catheter recited in claim 1 further comprising:
   first means for attaching the foam tip to the catheter body;
   second means for attaching the foam tip to the stylet; and
   the second means being disposed distally of the first means.

3. The catheter recited in claim 2, wherein:
   the first means is disposed exteriorly of the catheter body; and
   the second means is disposed interiorly of the foam tip.

4. The catheter recited in claim 2 wherein the catheter tip encloses the first end of the catheter body.

5. The catheter recited in claim 1 wherein the stylet is disposed interiorly of the catheter body and is retractable relative to the catheter body to enlarge the catheter tip at the first end of the catheter body.

6. The catheter recited in claim 1 wherein the foam tip has a low profile state and a high profile state and the catheter further comprises:
   spring means surrounding the stylet distally of the catheter body for maintaining the foam tip in one of the low profile state and the high profile stage.

7. The catheter recited in claim 1 wherein the foam tip has compression characteristics which vary generally linearly radially of the stylet.

8. A method for removing an embolus, thrombus, or other clot from a blood vessel, comprising the steps of:
   creating an opening into the blood vessel;
   inserting through the opening and into the blood vessel a catheter including a tubular catheter body, a catheter tip formed of a nonwoven foam material, and an actuator for deforming the catheter tip between an expanded state and a compressed state;
   advancing the catheter tip beyond the clot in the vessel;

manipulating the actuator to place the catheter tip in the expanded state;

moving the catheter tip toward the opening, the foam material in the tip having a tendency to compress upon engaging the clot; and during the moving step, resisting compression of the catheter tip with elastomeric forces created by the foam material, to avoid high pressures damaging to the blood vessel.

9. The method recited in claim 8 wherein during the resisting step the elastomeric forces produce pressures which are less than a magnitude damaging to the blood vessel.

10. The method recited in claim 9 wherein during the resisting step the elastomeric forces produce pressures which are generally free of pressure spikes damaging to the blood vessel.

11. The method recited in claim 9 wherein during the resisting step the elastomeric forces produce pressures which are generally linear throughout the moving step.

12. The method recited in claim 8 wherein during the inserting step the catheter is further characterized by an outer surface of the catheter body and the foam material is attached to the outer surface.

* * * * *